(12) United States Patent
Kissinger et al.

(10) Patent No.: US 9,204,833 B2
(45) Date of Patent: Dec. 8, 2015

(54) CARTRIDGE FOR AUTOMATED BLOOD SAMPLING SYSTEM

(75) Inventors: Peter T. Kissinger, West Lafayette, IN (US); Candice B. Kissinger, West Lafayette, IN (US)

(73) Assignee: Phlebotics, Inc., West Lafayette, IN (US)

( * ) Notice: Subject to any disclaimer, the term of this patent is extended or adjusted under 35 U.S.C. 154(b) by 698 days.

(21) Appl. No.: 13/431,377

(22) Filed: Mar. 27, 2012

(65) Prior Publication Data

US 2013/0261499 A1    Oct. 3, 2013

(51) Int. Cl.
*A61B 5/00* (2006.01)
*A61B 5/155* (2006.01)
*A61B 5/15* (2006.01)

(52) U.S. Cl.
CPC ............... *A61B 5/155* (2013.01); *A61B 5/1427* (2013.01); *A61B 5/15003* (2013.01); *A61B 5/150221* (2013.01); *A61B 5/150229* (2013.01); *A61B 5/150305* (2013.01)

(58) Field of Classification Search
CPC ................. A61B 5/155; A61B 5/1427; A61B 5/150221; A61B 5/15003
USPC ................................. 600/573; 604/403, 409
See application file for complete search history.

(56) References Cited

U.S. PATENT DOCUMENTS

| | | |
|---|---|---|
| 1,482,955 A | 2/1924 | Tideman |
| 4,077,395 A | 3/1978 | Woolner |
| 4,696,309 A | 9/1987 | Stephan |
| 4,747,414 A | 5/1988 | Brossel |
| 4,832,294 A | 5/1989 | Eidem |
| 4,883,068 A | 11/1989 | Dechow |
| 5,423,738 A | 6/1995 | Robinson et al. |
| 5,556,065 A | 9/1996 | Wadley |
| 5,569,287 A | 10/1996 | Tezuka et al. |
| 5,662,127 A | 9/1997 | De Vaughn |
| 5,716,008 A | 2/1998 | Nottingham et al. |
| 5,800,781 A | 9/1998 | Gavin et al. |
| 6,062,224 A | 5/2000 | Kissinger et al. |
| 6,183,442 B1 | 2/2001 | Athanasiou et al. |
| 6,261,245 B1 | 7/2001 | Kawai et al. |
| 6,368,563 B1 | 4/2002 | Allen et al. |
| 6,390,311 B1 | 5/2002 | Belokin |
| 6,402,704 B1 | 6/2002 | McMorrow |
| 6,547,755 B1 | 4/2003 | Himbert et al. |
| 6,663,835 B2 | 12/2003 | Allen et al. |
| 6,736,783 B2 | 5/2004 | Blake et al. |
| 6,793,633 B2 | 9/2004 | Douglas et al. |

(Continued)

FOREIGN PATENT DOCUMENTS

WO    WO 2006/033715 A3    3/2006

OTHER PUBLICATIONS

Thomas F Catron et al., A Strategy for Determining Arterial Blood Gases on the Summit of Mt. Everest, BMC Physiology, Mar. 2006, vol. 6, Issue 3, doi:10.1 186/1472-6793-6-3.

(Continued)

*Primary Examiner* — Max Hindenburg
*Assistant Examiner* — Jonathan M Foreman
(74) *Attorney, Agent, or Firm* — Faegre Baker Daniels LLP

(57) ABSTRACT

A cartridge for an automated blood sampling system for collecting samples and a method of sampling fluids from a test subject using an automated blood sampling apparatus including a cartridge are disclosed.

17 Claims, 8 Drawing Sheets

(56) References Cited

U.S. PATENT DOCUMENTS

| | | |
|---|---|---|
| 6,866,675 B2 | 3/2005 | Perez et al. |
| 6,899,851 B2 | 5/2005 | Allen et al. |
| 7,491,178 B2 | 2/2009 | Boecker et al. |
| 7,537,571 B2 | 5/2009 | Freeman et al. |
| 7,608,042 B2 | 10/2009 | Goldberger et al. |
| 7,608,223 B2 | 10/2009 | Berndtsson et al. |
| 7,708,701 B2 | 5/2010 | Boecker et al. |
| 7,780,610 B2 | 8/2010 | Sonoda et al. |
| 7,803,123 B2 | 9/2010 | Perez et al. |
| 7,875,047 B2 | 1/2011 | Freeman et al. |
| 7,892,183 B2 | 2/2011 | Boecker et al. |
| 8,021,631 B2 | 9/2011 | Ruhl et al. |
| 8,052,617 B2 | 11/2011 | Kissinger |
| 2002/0091454 A1 | 7/2002 | Vasko |
| 2005/0178218 A1 | 8/2005 | Montagu |
| 2006/0009727 A1 | 1/2006 | O'Mahony et al. |
| 2010/0145248 A1* | 6/2010 | Myrick et al. ............ 604/4.01 |
| 2011/0028862 A1 | 2/2011 | Hein et al. |
| 2011/0125058 A1 | 5/2011 | Levinson et al. |
| 2011/0160614 A1 | 6/2011 | Fujiwara et al. |
| 2011/0172510 A1 | 7/2011 | Chickering, III et al. |
| 2012/0010529 A1 | 1/2012 | Chickering, III et al. |
| 2013/0172711 A1 | 7/2013 | Tamir |
| 2013/0211289 A1 | 8/2013 | Moga et al. |

OTHER PUBLICATIONS

International Searching Authority, International Search Report for International Application No. PCT/US05/28141, Aug. 12, 2008.

International Searching Authority, Written Opinion for International Application No. PCT/US05/28141, Aug. 12, 2008.

International Searching Authority, International Preliminary Report on Patentability for International Application No. PCT/US05/28141, Oct. 21, 2008.

International Searching Authority, International Search Report and Written Opinion for PCT/US13/33781, mailed Jun. 13, 2013, 20 pages.

Jung et al., A micro blood sampling system for catheterized neonates and pediatrics in intensive care unit, Biomed Microdevices (2013), published online Nov. 14, 2012, Springer Science + Business Media, pp. 241-253.

* cited by examiner

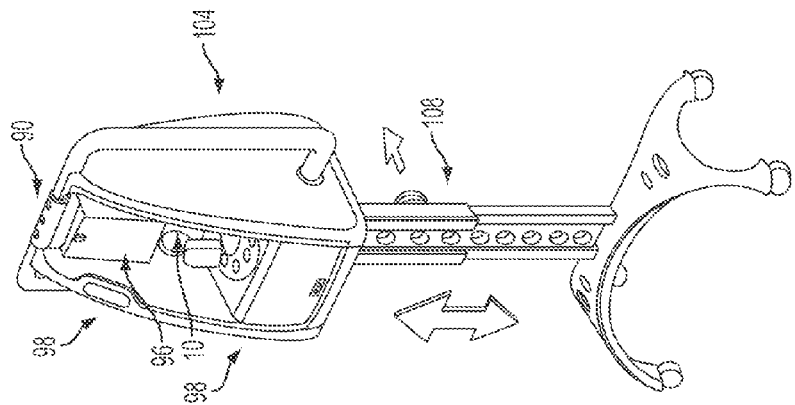
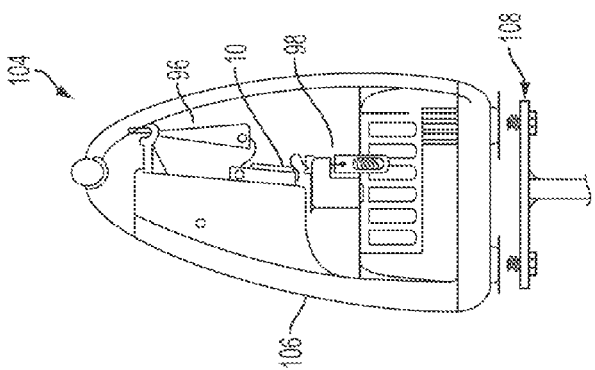
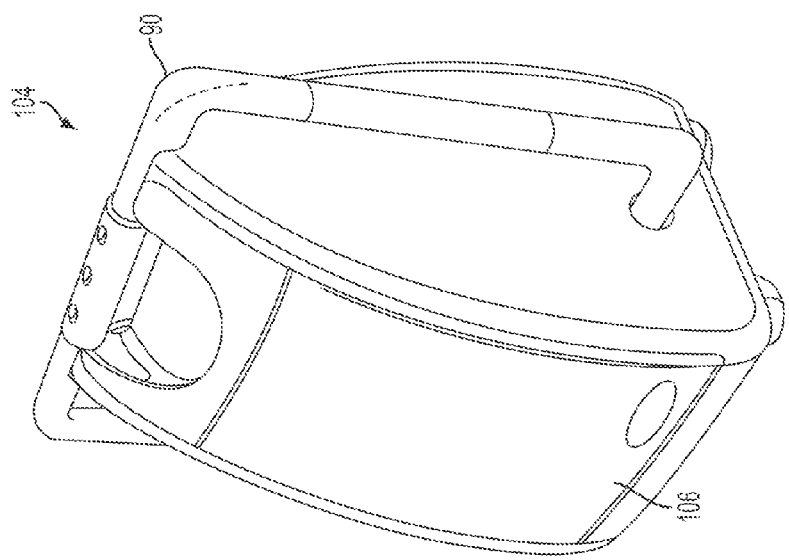

CARTRIDGE FOR AUTOMATED BLOOD SAMPLING SYSTEM

FIELD OF THE DISCLOSURE

The disclosure relates to a device for use in treating patients and performing biomedical research, and in particular to a system for automatically collecting serial blood samples from patients for diagnostic or research purposes.

BACKGROUND AND SUMMARY OF THE DISCLOSURE

Automated blood sampling ("ABS") is a method of automatically collecting serial blood or other fluid samples from a patient for diagnostic or research purposes. ABS reduces the trauma associated with multiple "sticks" (insertion of a needle into a vein or artery) during the repeated blood sampling that is necessary to monitor disposition of drug treatments. This may have particular relevance in sampling blood or other fluids from very young infants, such as those in neonatal or pediatric intensive care, who may have little blood to spare.

ABS has benefits in research, such as during Phase 1 and Phase 2 Clinical Trials (in association with electrocardiography, blood pressure recording, and body temperature monitoring). Automating the process of blood or fluid sampling potentially allows sampling to be done with greater temporal accuracy (i.e. the collection of samples at a specific time), allows for the use of less human personnel, and reduces the amount of fluid wasted compared to manual methods of acquiring the same samples and data. Automated blood sampling may also reduce the risk of infections, including nosocomial infections.

ABS units may also be provided in a portable embodiment. In some embodiments, the ABS unit includes a battery or other portable power source. The use of a portable ABS allows for greater mobility of the patient during sample collection. Patients may be able to go about daily activities, such as eating meals, sending emails, reading a book, and walking to a restroom, while attached to an ABS unit. Greater mobility and fewer sticks may lead to reduced stress. Stress involves the release of various hormones, and such hormones may affect the samples being collected in both human and non-human studies. U.S. Pat. No. 8,052,617 discloses an apparatus and a method for conducting automated blood sampling, the teachings of which are herein incorporated by reference.

Biomedical research techniques, such as infusion, in vivo microdialysis, in vivo ultrafiltration, in vivo electrochemistry, and electrocardiology study the performance of living organs, such as the brain, heart, circulatory system, muscles, etc. These techniques also require connections between one or more external devices and one or more sensors or implants in the body. Examples of devices include syringe pumps, fraction collectors, electrometers, vacuum sources, light sources, and potentiostats. Examples of implants include infusion cannulae, ultrafiltration probes, microdialysis probes, electrodes, and biosensors.

The present disclosure provides an apparatus and method for collecting a fluid sample from a subject for a test. In one exemplary embodiment, the test subject is an adult human. In another exemplary embodiment, the subject is a human child. As used herein, "test" may comprise collection of a fluid sample, as in automated blood sampling, sampling of another body fluid, or parallel acquisition of an electronic signal, such as during blood pressure or electrocardiogram monitoring. The fluid sample collected may be used in medical or clinical analysis of the patient for diagnostic or research purposes. In one embodiment, the sample collection and analysis are provided as a part of neonatal, pediatric or adult intensive care of the patient, including but not limited to military intensive care. In another embodiment, the sample collection and analysis are provided as a part of a personalized medicine regime or treatment. Example of personalized medicine treatment include, but are not limited to, measuring the circulating concentration of an administered drug or tracking the patient's chemical response to a drug. In still another embodiment, the sample collection and analysis are provided as a component of biomedical research. Those of skill in the art will recognize that the sample collection and analysis may also be provided as part of other medical or clinical processes.

In an exemplary embodiment, the disclosure provides a replaceable cartridge for an ABS apparatus. In another exemplary embodiment, a method of collecting a fluid sample from a test subject for a test using an ABS apparatus with a replaceable cartridge is provided.

In one embodiment, a cartridge for a fluid sampling apparatus for collecting a fluid sample from a test subject is provided. In an exemplary embodiment, the cartridge includes a pump, a reservoir fluidly connected to the pump, a first fitting for connecting the cartridge to a tubing sampling fluid from a test subject, a second fitting for connecting the cartridge to a sample collection component, and a third fitting for connecting the cartridge a sterile fluid supply, wherein the pump is configured to move in response to the fluid sampling apparatus and a plurality of valves controlling the flow between the reservoir, pump, and fittings. In another exemplary embodiment, the cartridge is a sterilized, disposable cartridge that can be replaced in the fluid sampling apparatus by a similar cartridge.

In another embodiment, a method for collecting a fluid sample from a test subject is provided. In an exemplary embodiment, the method includes coupling a cartridge to a fluid sampling apparatus, the cartridge comprising a pump, a reservoir, a reservoir fluidly connected to the pump, a first fitting for connecting the cartridge to a tubing sampling fluid from the test subject, a second fitting for connecting the cartridge to a sample collection component, and a third fitting for connecting the cartridge to a sterile fluid supply, wherein the pump is configured to move in response to the fluid sampling apparatus and a plurality of valves control flow between the reservoir, pump, and fittings. The exemplary embodiment also includes connecting the distal end of the tubing into the test subject, opening a first valve and moving the pump to draw sample fluid into the reservoir, opening a second valve and moving the pump to force fluid from the reservoir into the sample collection component, and flushing the fittings with sterile fluid, where the pump and valves are controlled by a controller. In another exemplary embodiment, the cartridge is disposable and can be simply and easily replaced with a sterile, disposable cartridge, reducing labor costs for health care providers.

In one exemplary embodiment, an ABS apparatus capable of receiving a cartridge is incorporated with a portable electric power supply into a wheeled neonatal intensive care unit (NICU) isolette or incubator or an intensive care unit (ICU) bed to enable sampling to continue while a patient is moved between rooms. In another exemplary embodiment, an ABS apparatus capable of receiving a cartridge is incorporated as a part of exercise physiology devices, including but not limited to treadmills and stationary bicycles, for stress tests such as stress electrocardiograms, and evaluation of athletes, patients, or members of the military. In still another exemplary embodiment, an ABS apparatus capable of receiving a cartridge is incorporated into a military long range pallet system used to air transport battle casualties.

In one embodiment, the ABS apparatus is used in a research application to anticipate a decline in patient status by collecting fluid samples and analyzing the samples, such as, but not limited to, determining blood gases, electrolytes, glucose, biomarkers, and drug or metabolite concentrations. In another embodiment, the ABS apparatus is used in a research, clinical, or treatment application to collect fluid samples over time to monitor and track the chemical response to an intervention.

The above mentioned and other features of the invention, and the manner of attaining them, will become more apparent and the invention itself will be better understood by reference to the following description of embodiments of the invention taken in conjunction with the accompanying drawings.

BRIEF DESCRIPTION OF THE DRAWINGS

The disclosure is explained in greater detail below in reference to the figures. In the figures:

FIG. 5 shows several views of another illustrative ABS apparatus with an ABS cartridge installed;

DETAILED DESCRIPTION OF THE DRAWINGS

The embodiments disclosed below are not intended to be exhaustive or to limit the invention to the precise forms disclosed in the following detailed description. Rather, the embodiments are chosen and described so that others skilled in the art may utilize their teachings. While the present disclosure is primarily directed to a portable sample or testing device for intensive care medicine, pharmacokinetics and physiology studies, it should be understood that the features disclosed herein may have application to collection of other types of samples.

Figure 1:
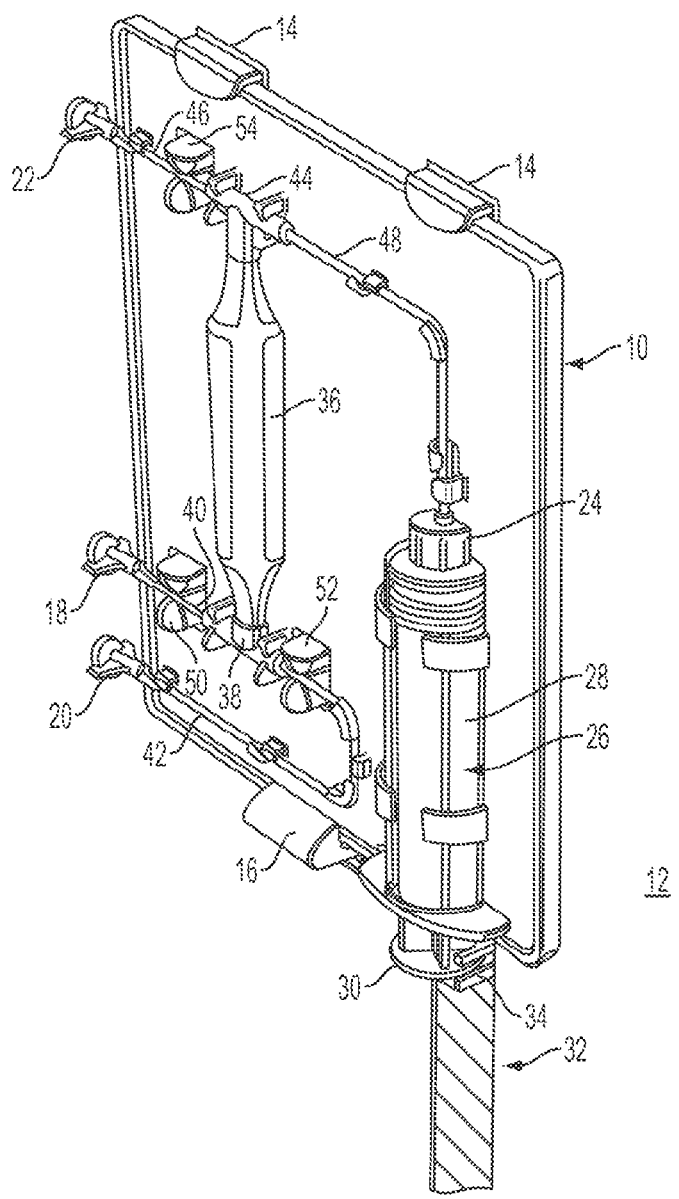
FIG. 1 shows an illustrative ABS cartridge attached to a portion of an ABS apparatus.

Referring to FIG. 1, an illustrative ABS cartridge 10 is shown attached to a portion of an ABS apparatus 12. In one exemplary embodiment, cartridge 10 is attached to ABS apparatus 12 using hooks 14 and latch 16. In the illustrated embodiment, cartridge 10 is inserted into hooks 14, latch 16 is depressed, cartridge 10 is pushed in toward ABS apparatus 12 and latch 16 snaps into position. In another embodiment, cartridge 10 is attached to ABS apparatus 12 using a plurality of hooks 14. In still another embodiment, cartridge 10 is attached to ABS apparatus 12 using a plurality of latches 16. Other suitable methods of removably attaching cartridge 10 to ABS apparatus 12, including but not limited to grooves, snaps, and rotatable clasps may also be used.

Cartridge 10 includes a plurality of connectors. In the exemplary embodiment illustrated in FIG. 1, first connector 18 connects cartridge 10 to a catheter conduit, which has a distal end inserted into the test subject from which the sample is to be collected. Although the test subject from whom the sample is to be collected in one exemplary embodiment is a human, in other embodiments fluid samples may be taken from other animals. Second connector 20 connects cartridge 10 to a sample collection container or fraction collector for collecting and storing samples. Third connector 22 connects cartridge 10 to a saline bag or other physiologically compatible solution, such as, but not limited to Ringer's solution. In another exemplary embodiment, syringe connector 24 connects cartridge 10 to syringe pump 26. In still another exemplary embodiment, syringe pump 26 is provided as part of cartridge 10. As illustrated, connectors 18, 20, 22, 24 are fluid fittings. In one exemplary embodiment, connectors 18, 20, 22, 24 are leak-free connections such as Luer lock style connectors. Exemplary Luer lock connectors are Luer-Lok™ connectors available from Becton Dickinson & Co., Franklin Lakes, N.J. Other suitable fluid fittings may also be used.

In the exemplary embodiment illustrated in FIG. 1, syringe pump 26 is provided as part of cartridge 10. Syringe pump 26 includes barrel 28 and plunger 30. ABS apparatus 12 includes syringe mechanism 32. Syringe mechanism connector 34 connects syringe mechanism 32 to plunger 30 such that movement of syringe mechanism 32 moves plunger 30. In the exemplary embodiment illustrated in FIG. 1, connector 34 attaches above and below one end of plunger 30. Other connections are also contemplated. For example, plunger 30 may include a groove into which connector 34 is inserted, or a portion of plunger 30 and connector 34 may comprise a key and slot that allow plunger 30 to move in response to movement from syringe mechanism 32. In one exemplary embodiment, syringe pump 26 may comprise the Culex ABS syringe drive manufactured by Bioanalytical Systems, inc. of West Lafayette, Ind. In other embodiments, syringe pump 26 is another means for moving fluid including, but not limited to, a reciprocal piston pump, a peristaltic pump, or a vacuum or pressure source.

In another exemplary embodiment, syringe pump 26 is not provided as part of cartridge 10, but is connected to cartridge 10 through syringe connector 24 and to a portion of ABS apparatus 12 through syringe mechanism connector 34.

Cartridge 10 includes fluid reservoir 36. In the exemplary embodiment illustrated in FIG. 1, reservoir 36 is a container into which fluid can be received and dispensed. In another exemplary embodiment, fluid reservoir 36 is an enlarged section of conduit or tubing. In still another exemplary embodiment, fluid reservoir 36 is an extended length of conduit or tubing. In still yet another exemplary embodiment, fluid reservoir is integrally formed with cartridge 10.

A first end of reservoir 36 is fluidly connected to first intersection or T connector 38. T connector 38 fluidly connects reservoir 36 to first connector 18 through catheter conduit 40 and second connector 20 through collector conduit 42.

A second end of reservoir 36 is fluidly connected to second intersection or T connector 44. T connector 44 fluidly connects reservoir 36 to third connector 22 through reservoir conduit 46 and syringe pump 26 through syringe conduit 48.

Although the exemplary embodiment of cartridge 10 illustrated in FIG. 1 shows reservoir 36 as a vertically oriented container attached to first T connector 38 below reservoir 36 and attached to second T connector 44 above reservoir 36, other orientations are also contemplated, including but not limited to horizontal connections of first and second T connectors 38, 44 with reservoir 36 and reversing the positions of first and second T connectors 38, 44.

In the exemplary embodiment illustrated in FIG. 1, catheter conduit 40 is routed through first valve 50, collector conduit 42 is routed through second valve 52, and reservoir conduit 46 is routed through third valve 54. In one embodiment, valves 50, 52, 54 are operably connected to ABS apparatus 12.

Figure 2C:
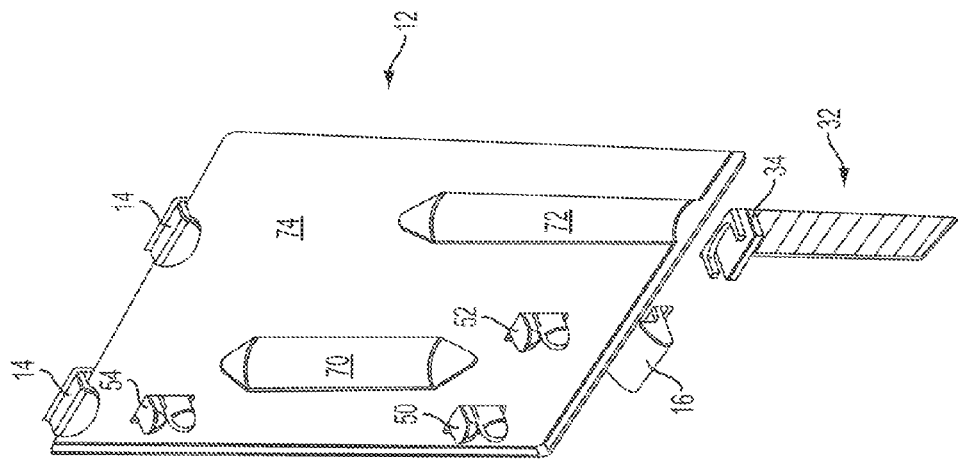
FIG. 2 shows an exploded view of the ABS cartridge and ABS apparatus portion of FIG. 1.
Figure 2B:
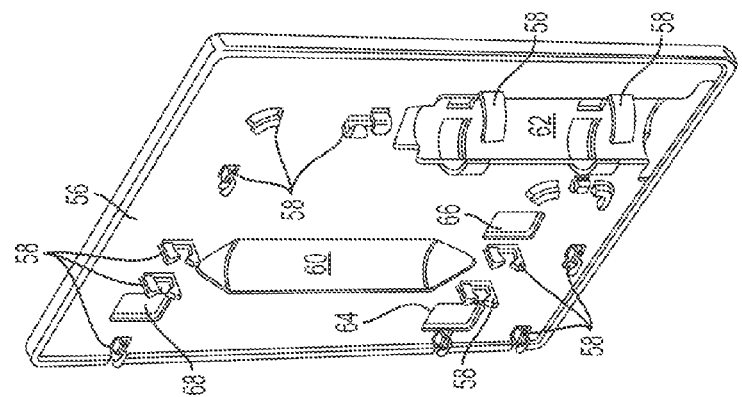
Figure 2A:
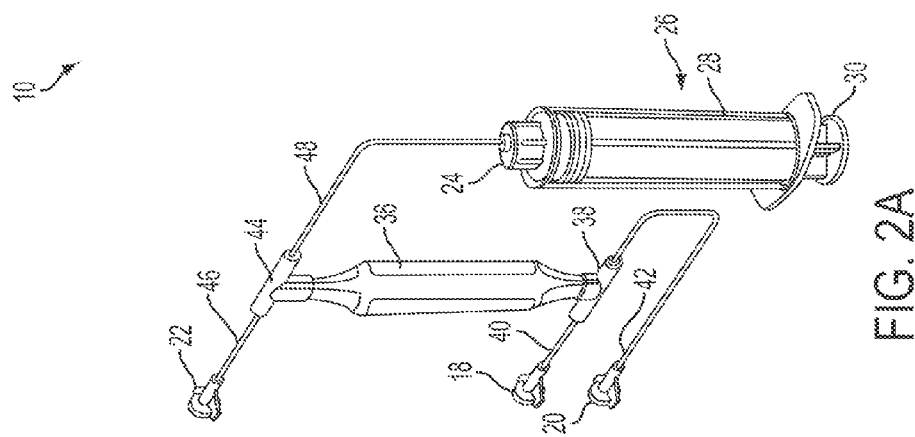

Referring next to FIG. 2, an exploded view of cartridge 10 and ABS apparatus 12 of FIG. 1 is illustrated. FIG. 2A illustrates a portion of one exemplary embodiment of cartridge 10 including connectors 18, 20, 22, 24, syringe pump 26, reservoir 36, T connectors 38, 44, and conduit 40, 42, 46, 48. FIG. 2B illustrates another portion of the exemplary embodiment of cartridge 10 including cartridge frame 56. FIG. 2C illustrates a portion of one exemplary embodiment of ABS apparatus 12 for receiving cartridge 10 including hooks 14, latch 16, syringe mechanism 32, and valves 50, 52, and 54.

In the exemplary embodiment illustrated in FIGS. 1 and 2, cartridge frame 56 includes a plurality of snap and routing supports 58. Snap and routing supports 58 support cartridge components on frame 56. The plurality of snap and routing supports 58 may include clamps, guides, snaps, and supports. As shown in FIG. 2B, snap and routing supports 58 may be formed as part of cartridge frame 56. In another embodiment, snap and routing supports 58 may be attached to cartridge frame 56. Snap and routing supports 58 may be formed from a plastic or other polymeric material. Those of skill in the art will recognize that other materials may also be used. In one embodiment, snap and routing supports 58 support at least one of conduit 40, 42, 46, 48. In another embodiment, snap and routing supports 58 support at least one of T connectors 38, 44. In still another embodiment, snap and routing supports 58 support syringe barrel 28.

Referring to FIG. 2B, in one exemplary embodiment, cartridge frame 56 includes recesses 60, 62, for receiving reservoir 36 and syringe pump 26. In another exemplary embodiment, at least one of recesses 60, 62 are cut-outs.

In the exemplary embodiment illustrated in FIG. 2B, cartridge frame 56 includes first valve window 64 for receiving valve 50, second valve window 66 for receiving valve 52, and third valve window 68 for receiving valve 54 from ABS apparatus 12. In another embodiment, more than one valve may be positioned in a window.

In one exemplary embodiment, valves 50, 52, and 54 are pinch valves that fit around conduits 40, 42, 46 and restrict or prevent fluid flow through conduits 40, 42, 46 in a closed state and allow fluid flow through conduits 40, 42, 46 in an open state. In one embodiment, valves 50, 52, and 54 include rod-like elements that fit around conduits 40, 42, 46. In the open state, the rod-like elements are positioned to allow fluid to flow through conduits 40, 42, 46. In the closed state, a force is applied to a first of the rod-like elements causing it to move toward the second of the rod-like elements, squeezing the conduits 40, 42, 46 between the rod-like elements and restricting or preventing fluid flow. In another embodiment, force is applied to both of the rod-like elements. Force may be applied to the rod-like elements through the use of a motor and cam, a linear actuator, a pneumatic actuator, a solenoid, or other suitable methods.

In another exemplary embodiment, valves 50, 52, 54 are telescoping style pinch valves. Telescoping style pinch valves have an open state that allows fluid flow through conduits 40, 42, 46 and a closed state in which a valve element is driven from ABS apparatus 12 into contact with a conduit 40, 42, 46 and against a corresponding stationary element of cartridge frame 56 positioned opposite the conduit 40, 42, 46 from the driven valve element to restrict or prevent fluid flow through the conduit 40, 42, 46.

Other suitable fluid control means can be used in place of the illustrated valves. For example, first valve 50 and second valve 52 may be replaced by a single three-way valve. Additionally, valves 50, 52, 54 may be in-line valves. In another embodiment, pump 26 is connected to syringe conduit 48 connects syringe pump 26 to reservoir 36 through a three way connector with catheter conduit 40 and collector conduit 44 in place of first T connector 38. Other suitable valves may also be used.

In another exemplary embodiment, some elements of cartridge 10 are integrally formed with cartridge frame 56. In one embodiment, at least one of reservoir 36, connectors 18, 20, 22, 24, syringe barrel 28, T connectors 38, 44, and snap and routing supports 58 are formed as part of cartridge frame 56. In another embodiment, at least one of conduits 40, 42, 46, 48 is at least partially formed as part of cartridge frame 56 and valves 50, 52, 54 control flow by applying a force to a portion of conduit 40, 42, 46, 48 causing the conduit to deform and restrict or prevent fluid flow. In still another embodiment, at least one of reservoir 36, conduit 40, 42, 46, 48, connectors 18, 20, 22, 24, syringe barrel 28, and T connectors 38, 44 are integrally formed together and secured to frame 56 prior to cartridge 10 being operably connected to ABS apparatus 12.

Referring to FIG. 2C, in one exemplary embodiment, ABS apparatus 12 includes recesses 70, 72, for receiving reservoir and syringe pump recesses 60, 72. In another exemplary embodiment, at least one of recesses 70, 72 directly receives reservoir 36 or syringe pump 26. In the embodiment illustrated in FIG. 2C, ABS apparatus 12 includes cartridge recess 74 for receiving cartridge 10. Cartridge 10 is secured in recess 74 by hooks 14 and latch 16.

In one exemplary embodiment, cartridge 10 and ABS apparatus 12 cooperate to allow installation of cartridge 10 into ABS apparatus 12 in only one orientation. In the embodiment illustrated in FIGS. 1 and 2, recesses 70, 72 will receive cartridge 10 in only one orientation, and syringe mechanism 32 will only receive plunger 30 in the same orientation. Other methods of allowing installation in only one orientation are also contemplated. For example, in another embodiment, cartridge frame 56 and cartridge recess 74 are shaped to only allow installation of cartridge 10 in one orientation. In still another embodiment, cartridge frame 56 is shaped so that hooks 14 and latch 16 only engage cartridge frame 56 in one orientation.

Figure 3:
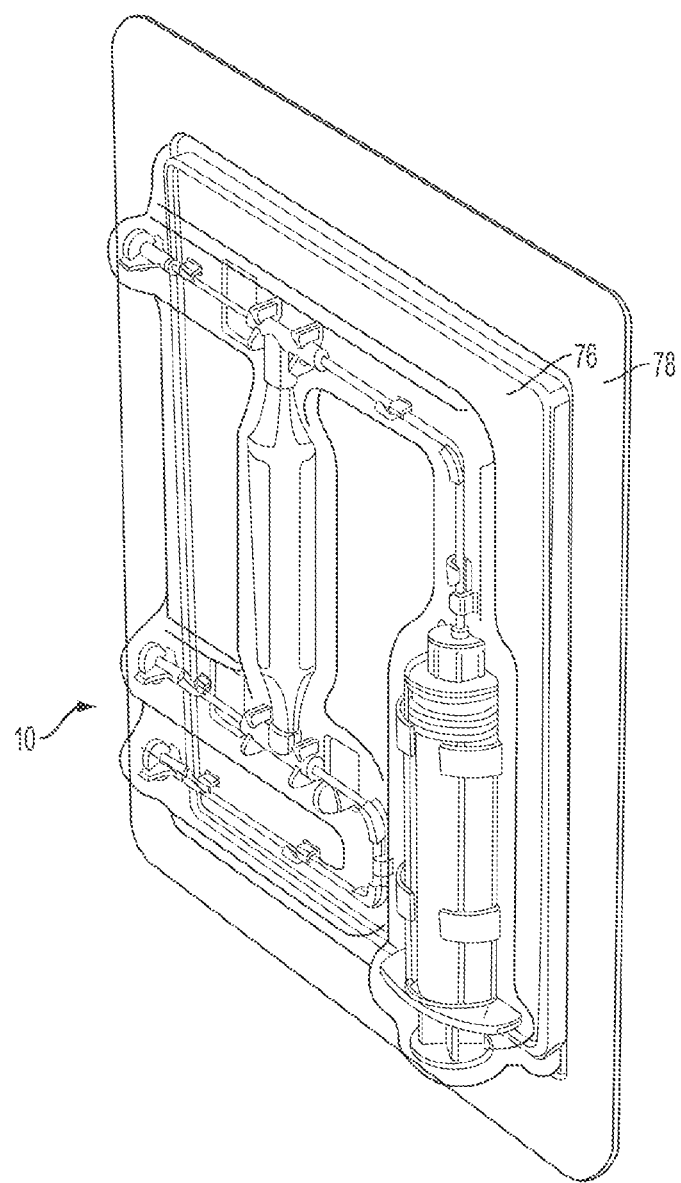
FIG. 3 shows an illustrative ABS cartridge packaged in a blister pack.

Referring next to FIG. 3 the exemplary cartridge 10 of FIGS. 1 and 2 is illustrated packaged in blister pack 76. In one exemplary embodiment, blister pack 76 is a sterile blister pack, and cartridge 10 is packed in sterile blister pack 76 and opened when ready to be used. Blister pack 76 includes cardboard perimeter 78. Cardboard perimeter 78 makes the packaging of blister pack 76 more robust and allows space for printing critical and branding information. In one exemplary embodiment, cartridge 10 is sterilized using Food and Drug Administration approved sterilization procedures.

In one embodiment, providing a cartridge 10 for use with ABS apparatus 12 allows easier changeover of ABS apparatus 12 between patients. In another embodiment, ABS apparatus 12 is used to collect samples from multiple patients when cartridge 10 and tubing for collecting samples from the test subject are replaced for each patient. In still another embodiment, use of a new sterile cartridge 10 provided in blisterpack 76 for each test results in less cross contamination between tests. In one embodiment, a single cartridge 10 is used with an ABS apparatus 12 for collecting samples for up to two weeks on an individual patient. Used cartridge 10 is then replaced with a second sterile cartridge 10 for additional sampling. Longer or shorter durations may also be used, depending on the particular application.

Figure 8:
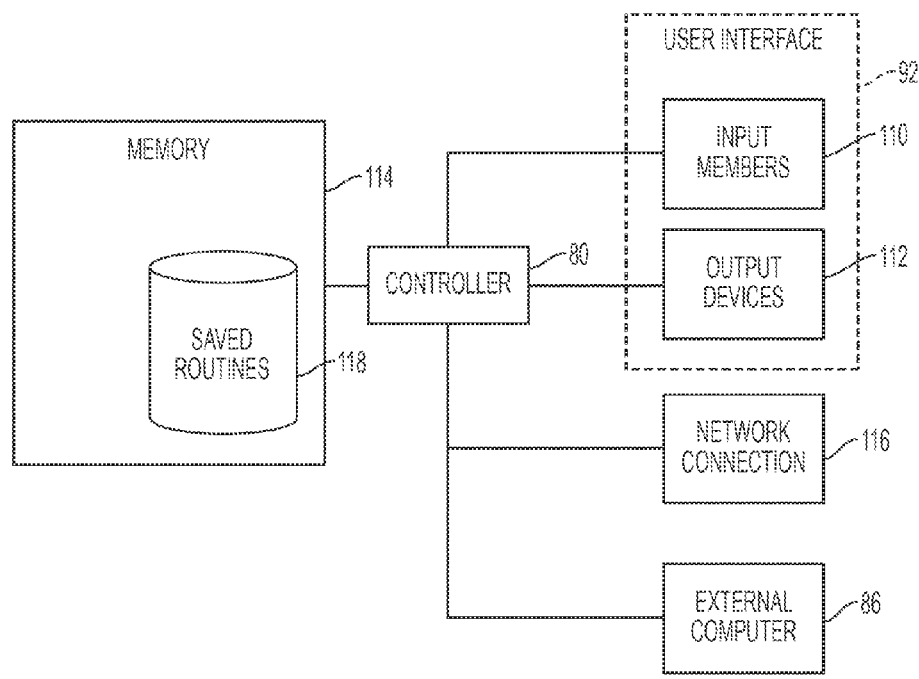
FIG. 8 illustrates an exemplary controller of the ABS apparatus of FIG. 1.

When installed in ABS apparatus 12, cartridge 10 cooperates with ABS apparatus 12 to provide automated fluid sampling. ABS apparatus 12 includes controller 80, which is operatively connected to valves 50, 52, 54, syringe mechanism 32, and sample fraction collector 82. An exemplary controller is illustrated in FIG. 8. Controller 80 may be a single controller or multiple controllers. Controller 80 may implement programming implemented as electrical circuits, software being executed by a processing unit, a combination thereof, or any other suitable configuration of software and/or software enabled hardware. In one embodiment controller 80 comprises a computer chip with embedded software code. In another embodiment, controller 80 is operably connected with user interface 92. In one embodiment, user interface 92 includes input members 110 and output members 112. Exemplary input members 110 include buttons, switches, keys, a touch display, a keyboard, a mouse, and other suitable devices for providing information to controller 80. Exemplary output devices 112 include lights, a display (such as a touch screen), printer, speaker, visual devices, audio devices, tactile devices, and other suitable devices for presenting information to an operator. In another embodiment controller 80 operably transfers information to and receives information from an external computer 86.

In another embodiment, controller 80 includes memory 114. Memory is a computer readable medium and may be a single storage device or may include multiple storage devices, located either locally with controller 80 or accessible across a network. Computer-readable media may be any available media that may be accessed by controller 80 and includes both volatile and non-volatile media. Further, computer readable-media may be one or both of removable and non-removable media. By way of example, computer-readable media may include, but is not limited to, RAM, ROM, EEPROM, flash memory or other memory technology, CD-ROM, Digital Versatile Disk (DVD) or other optical disk storage, magnetic cassettes, magnetic tape, magnetic disk storage or other magnetic storage devices, or any other medium which may be used to store the desired information and which may be accessed by controller 80. In one embodiment, controller 80 communicates data, status information, or a combination thereof to a remote device for analysis. In another embodiment, memory may further include operating system software, such as WINDOWS operating system available from Microsoft Corporation of Redmond, Wash. Memory further includes communications software if computer system has access to a network through a network connection 116, such as a local area network, a public switched network, a CAN network, and any type of wired or wireless network. Any exemplary public switched network is the Internet. Exemplary communications software includes e-mail software, internet browser software. Other suitable software which permit controller 80 to communicate with other devices across a network may be used.

In one exemplary embodiment, controller 80 controls the status of first valve 50 to control flow through catheter conduit 40, controls the status of second valve 52 to control flow through collector conduit 42, controls the status of third valve 54 to control flow through reservoir conduit 46; controls the movement of syringe pump 26 in a first direction drawing fluid into barrel 28 and a second direction forcing fluid from barrel 28; and instructs a sample fraction collector 82 to either receive fluid samples in vials 84 or to pass the fluid into a drain. In another embodiment, controller 80 is operatively connected to external computer 86.

Figure 4A:
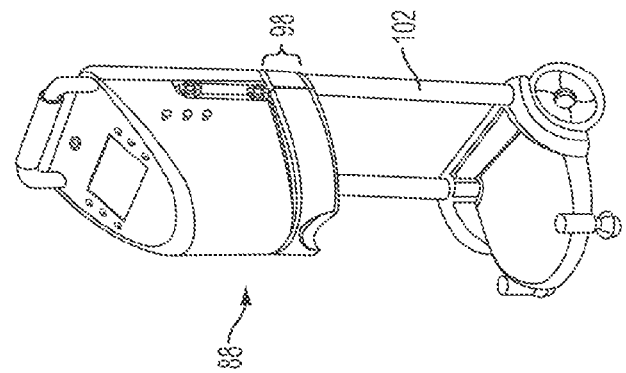
FIG. 4 shows several views of an illustrative ABS apparatus with an ABS cartridge installed.

Referring next to FIG. 4, several views of an illustrative ABS apparatus are provided. FIG. 4A illustrates a perspective view of the front of an ABS apparatus 88. The exemplary ABS apparatus 88 in FIG. 4A includes handle 90 with a soft touch cover, user interface 92, and hooks 94 for attaching saline bag 96 or other physiologically compatible solution. First connector 18 and third connector 22 of cartridge 10 can be seen extending out the side of ABS apparatus 88.

Sample collection area 98 is provided in the bottom of ABS apparatus 88. In one embodiment, sample collection area may be refrigerated using Peltier cooling. In another embodiment, sample collection area 98 includes instruments for analyzing collected samples, such as for point of care testing, near patient testing, or nursing stations. Exemplary instruments for analyzing collected samples include the Cobas c and other point of care, bedside testing and near patient systems available from Roche Diagnostics, Indianapolis, Ind., the i-STAT (R) System available from Abbott Laboratories, Abbott Park, Ill., and point of care systems available from Siemens healthcare Diagnostics Inc., Tarrytown, N.Y. Other suitable instruments for analyzing collected samples, such as but not limited to mass spectrometers, may also be used. In yet another embodiment, sample collection area stores samples in vials or cartridges for later testing and analysis. In still yet another embodiment, samples may be deposited on or absorbed in a matrix such as cellulose, open foam polymer, or ceramics from which the sample will later be retrieved. In another embodiment, samples are stored as dried blood samples on Guthrie cards.

Figure 4B:
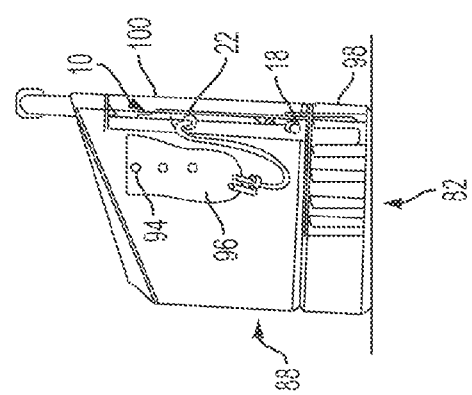

As shown in the exemplary embodiment illustrated in FIG. 4B, saline bag 96 can be attached to hook 94 and fluidly connected to third connector 22. In FIG. 4B, ABS apparatus 88 includes back panel 100. Back panel 100 may be removed from ABS apparatus 88, cartridge 10 may be installed, and back panel 100 may be replaced with access to first connector 18 and third connector 22 of cartridge 10 provided on the side of ABS apparatus 88.

Figure 4C:
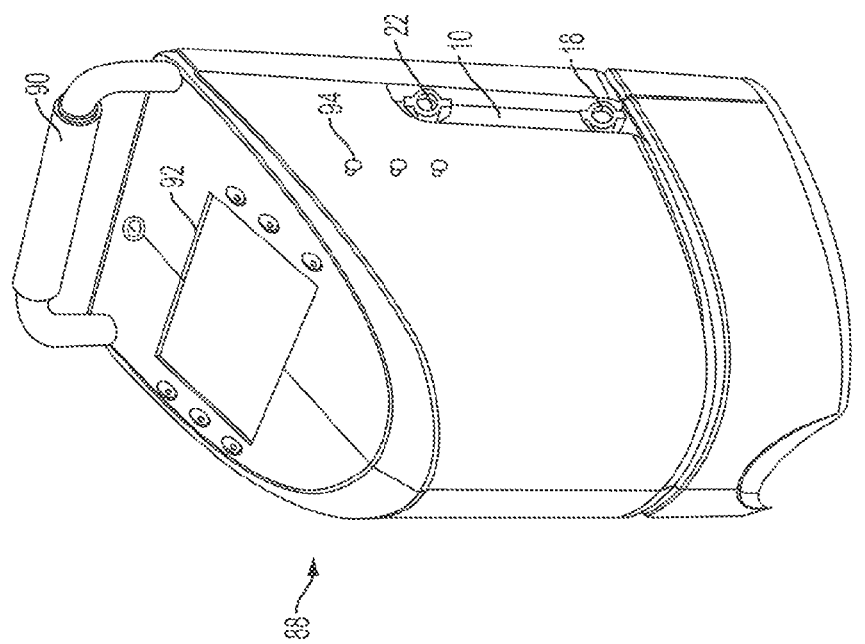

As shown in FIG. 4C, ABS apparatus 88 may be provided on wheeled stand 102. In the exemplary embodiment illustrated in FIG. 4C, the sample collection area 98 is removable from ABS apparatus 88 when ABS apparatus 88 is attached to wheeled stand 102.

Referring next to FIG. 5, several views of another illustrative ABS apparatus are provided. FIG. 5A illustrates a perspective view of the front of an ABS apparatus 104. The exemplary ABS apparatus 104 includes handle 90 and front panel 106. As shown in FIG. 5A, front panel 106 may be discrete to be non-invasive for the patient from whom the sample is being taken.

As shown in FIGS. 5B and 5C, a saline bag 96 or other physiologically compatible solution along with the remainder the sampling mechanism are provided behind front panel 106 and are accessible from the back side of ABS apparatus 104. Cartridge 10, and sample collection area 98 can be accessed by a technician. Additionally, ABS apparatus 104 may be provided on an adjustable stand 108 including casters for easy movement.

Although the position and orientation of components of cartridge 10 and ABS apparatus 12 have been illustratively described, those of skill in the art will recognize that other suitable positions and orientations may be used. In some embodiments, the test subject from which the sample is taken from may influence the design.

In one embodiment, cartridge 10 and ABS apparatus 12 may include a wheeled stand to allow the test subject to remain ambulatory while testing. In another embodiment for testing very young infants, cartridge 10 and ABS apparatus 12 have components with smaller volumes than for embodiments for testing adults. In still another exemplary embodiment, ABS apparatus 12 including a portable electric power supply is incorporated into a wheel neonatal intensive care unit (NICU) isolette or incubator or an intensive care unit (ICU) bed to enable sampling to continue while a patient is moved between rooms. In yet still exemplary embodiment, ABS apparatus 12 capable is incorporated as a part of exercise physiology devices, including but not limited to treadmills and stationary bicycles, for stress tests such as stress electrocardiograms, and evaluation of athletes, patients, or members of the military. In another exemplary embodiment, ABS apparatus 12 is incorporated into a military long range pallet system used to air transport battle casualties.

Other suitable designs depending on the subject to be tested may also be used.

Figure 6:
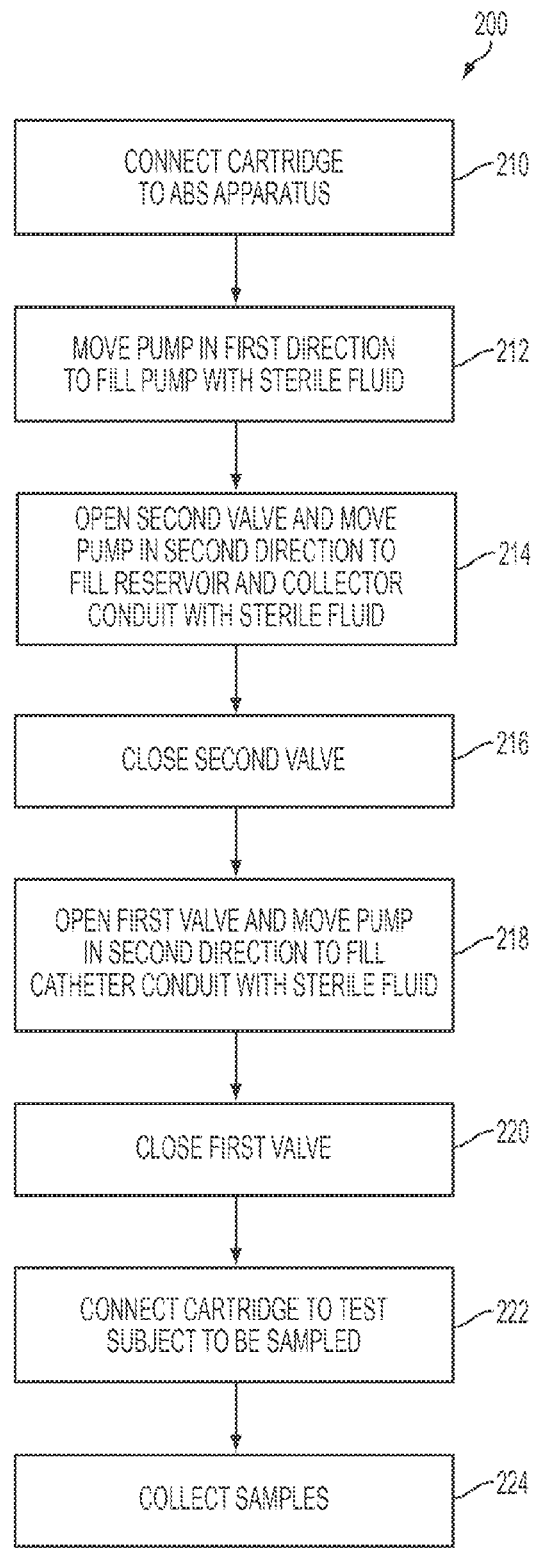
FIG. 6 illustrates an exemplary processing sequence for preparing an ABS apparatus and ABS cartridge for sampling.

FIG. 6 illustrates an exemplary processing sequence 200 for preparing an ABS apparatus 12 and ABS cartridge 10 for sampling. Although an exemplary sequence 200 is described for the exemplary ABS cartridge 10 and ABS apparatus 12 illustrated in FIG. 1, other suitable sequences may also be used.

In block 210, ABS cartridge 10 is operably connected to ABS apparatus 12. In one embodiment, operatively connecting ABS cartridge 10 to ABS apparatus 12 includes at least one of: positioning ABS cartridge 10 in cartridge recess 74; securing cartridge 10 with hooks 14 and latch 16; fluidly connecting first connector 18 to catheter conduit which has a distal end to be inserted into a subject; fluidly connecting second connector 20 to a sample collection container or fraction collector 82 for collecting and storing samples; fluidly connecting third connector 22 to a saline bag 96 or other physiologically compatible solution; and attaching syringe plunger 30 to syringe mechanism connector 34. Other suitable steps for operably connecting ABS cartridge 10 to ABS apparatus 12 may be used depending on the design of the components used.

Prior to block 212, first valve 50 and second valve 52 are closed and third valve 54 is opened. In block 212, syringe pump 26 is moved in a first direction to fill syringe pump 26 with sterile fluid from the saline bag 96. Moving syringe pump 26 in a first or second direction may include moving plunger 30 directly or moving syringe mechanism 32 connected to plunger 30 through syringe mechanism connector 34.

Third valve 54 is then closed, and in block 214, second valve 52 is opened and pump 26 is moved in a second direction to fill reservoir 36 and collector conduit 42 with sterile fluid. In block 216, second valve 52 is closed. In block 218, first valve 50 is opened and pump 26 is moved in a second direction to fill catheter conduit 40 with sterile fluid. First valve 50 is closed in block 220. ABS cartridge 10 is then ready to be connected to the test subject to be sampled, as shown in block 222. If first connector 18 has not been connected to sample tubing, that step can be done at this point. Sample tubing is positioned to collect sample fluid from the test subject, and samples are collected in block 224. Block 224 may include at least a portion of exemplary sequence 300.

Figure 7:
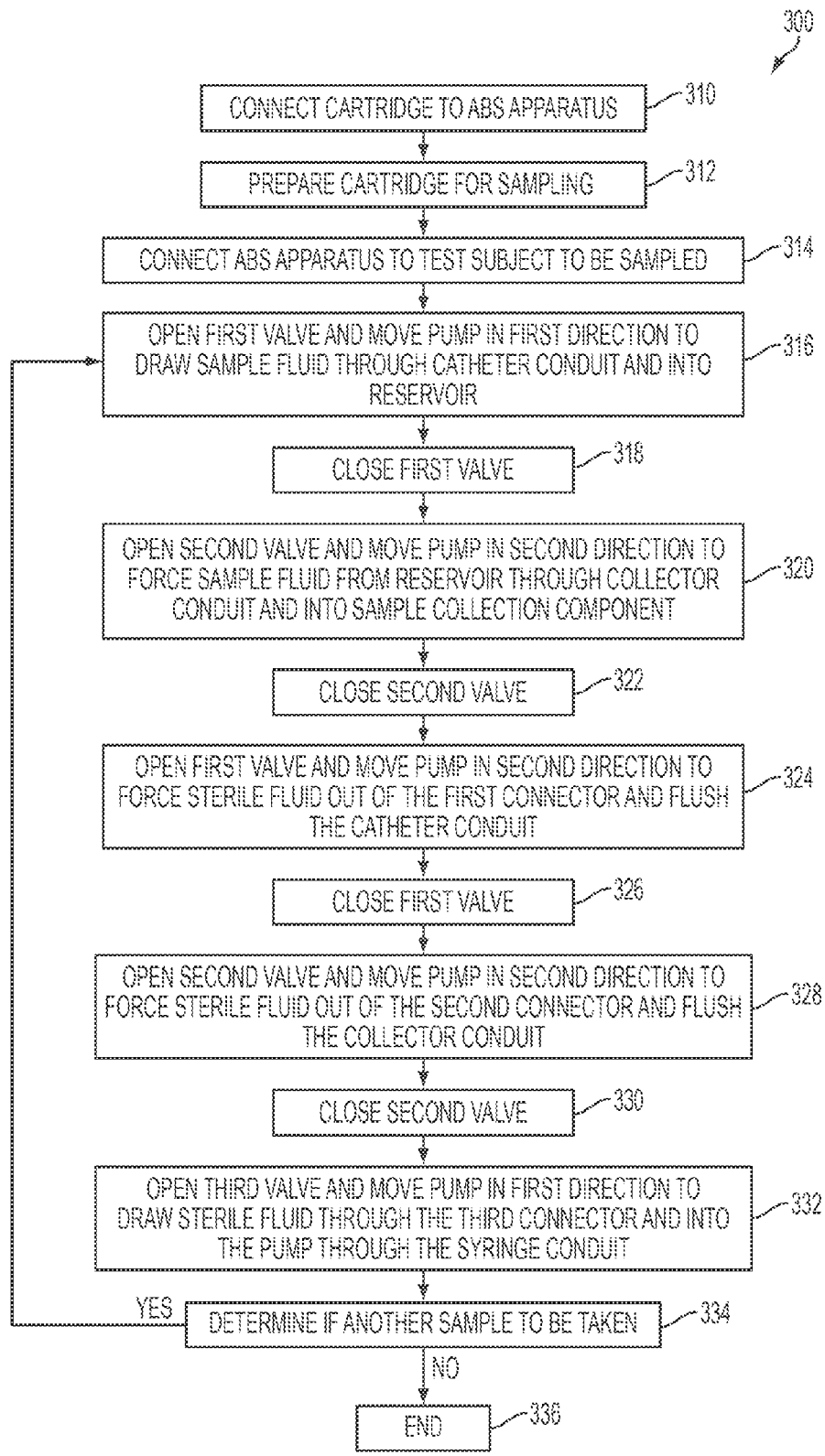
FIG. 7 illustrates an exemplary processing sequence for taking samples using an ABS apparatus and ABS cartridge.

FIG. 7 illustrates an exemplary processing sequence for taking samples using an ABS apparatus 12 and ABS cartridge 10. Although an exemplary sequence 300 is described for the exemplary ABS cartridge 10 and ABS apparatus 12 illustrated in FIG. 1, other suitable sequences may also be used. In block 310, ABS cartridge 10 is operably connected to ABS apparatus 12. In one embodiment, block 310 includes the same steps as block 210. In block 312, ABS cartridge 312 is prepared for sampling. In one embodiment, block 312 includes at least a portion of exemplary sequence 200. In block 314, ABS apparatus 12 is connected to the subject to be sampled. In one embodiment, block 314 includes the same steps as block 222.

In block 316, valves 54 and 52 are closed if open, and first valve 50 is opened. Pump 26 is moved in a first direction to draw sample fluid from the test subject being sampled through first connector 18, catheter conduit 40, first "T" connector 38, and into reservoir 36. First valve 50 is closed in block 318.

In block 320, second valve 52 is opened and pump 26 is moved in a second direction to force sample fluid from reservoir 36 through first T connector 38, through collector conduit 42 and second connector 20 into sample collection component 82. Second valve 52 is closed in block 322.

In block 324, first valve 50 is opened and pump 26 is moved in a second direction to force sterile fluid out of first connector 18 and flush catheter conduit 40. Block 324 may also return sample fluid to the subject through the sample tubing. First valve 50 is then closed in block 326.

In block 328, second valve 52 is opened and pump 26 is moved in a second direction to force sterile fluid out of the second connector 20 and flush collector conduit 42. Second valve 52 is then closed in block 330.

In block 332, third valve 54 is opened and pump 26 is moved in a first direction to draw sterile fluid from saline bag 96 through third connector 22 and into pump 26 through syringe conduit 48. Third valve 54 may then be closed.

In block 334, ABS apparatus 12 checks to see if another sample is to be taken. If another sample is called for, the sequence returns to block 316. If no other sample is called for, the sequence ends in block 336. The decision in block 334 may be made by controller 80, external computer 86, or through user interface 92 based on the desired sampling parameters.

If, at any time in sequence 200 or sequence 300, there is insufficient fluid in syringe pump 26, pump 26 can be refilled by closing valves 50, 52, opening valve 54 and moving pump 26 in a first direction to draw fluid into barrel 28. Additionally, before or after this step, second valve 52 may be opened and pump 26 may be moved in a second direction to expel sample fluid from the reservoir 36, T connectors 38, 44 and conduit 42, 48. If at any time in sequence 200 or sequence 300, there is too much fluid in syringe 26, thereby preventing syringe pump 26 from moving in a first direction because barrel 28 is already full, excess fluid can be purged by opening only second valve 52 and moving pump 26 in a second direction to expel sample fluid from pump 26.

The frequency and volumes of samples taken from the test subject depend on the needs of the test and decisions of medical personnel. In one exemplary embodiment, samples are collected from the test subject at a regular frequency of about every 60 seconds to every several hours. In another exemplary embodiment, samples are collected at predetermined times, a predetermined regular frequency, a variable time, or some combination stored in memory or programmed by the controller. In yet another exemplary embodiment, a sample will be collected upon a signal from ABS apparatus 12. In one exemplary embodiment, sample volumes of about 25 µL to about 4 mL are collected. In another exemplary embodiment, sample volumes of about 5 µL to about 4 mL are collected. In still another exemplary embodiment, sample volumes of less than about 5 µL are collected. In yet still another exemplary embodiment, sample volumes of about 4 mL to about 10 mL or more are collected. Other frequencies and volumes than those presented may also be used. In one exemplary embodiment, a log file identifying at least one of the patient, sample, caregiver, and time taken are recorded by ABS apparatus 12 in memory 114. In another exemplary embodiment, frequency and volume are selected from several options presented on user interface 92. In still another exemplary embodiment, a saved routine 118 including frequency and volume settings stored in memory 114 is selected from several options presented on user interface 92. The features of the disclosure disclosed in the above description, the claims and the figures can be of importance individually as well as in any combination for the realization of the disclosure in its various embodiments.

What is claimed is:

1. A cartridge for a fluid sampling device for collecting a fluid sample from a test subject, including:
   a pump being moveable in a first direction to draw fluid into the pump and a second direction to expel fluid from the pump;
   a reservoir in fluid communication with the pump;
   a first conduit fluidly connecting the reservoir to a first fluid fitting configured to fluidly connect the cartridge to a tubing having a distal end inserted into the subject;
   a second conduit fluidly connecting the reservoir to a second fluid fitting configured to connect the cartridge to a sample collection component; and
   a third conduit fluidly connecting the reservoir to a third fluid fitting configured to connect the cartridge to a sterile fluid supply;
   wherein the pump is configured to move in the first direction and second direction in response to movement of a portion of the fluid sampling device when the cartridge is operably connected to the fluid sample device and the fluid conduits are configured such that when the cartridge is operably connected to the fluid sampling device, a first valve of the fluid sampling device controls fluid flow in the first fluid conduit, a second valve of the fluid sampling device controls fluid flow in the second fluid conduit, and a third valve of the fluid sampling device controls fluid flow in the third fluid conduit;
   wherein the cartridge includes at least one window through a frame configured to allow the first valve of the fluid sampling device to extend through the frame to control fluid flow in the first fluid conduit by applying compressive force to the first fluid conduit, the second valve of the fluid sampling device to extend through the frame to control fluid flow in the second fluid conduit by applying compressive force to the second fluid conduit, and the third valve of the fluid sampling device to extend through the frame to control fluid flow in the third fluid conduit by applying compressive force to the third fluid conduit, and
   wherein the pump, reservoir, and fluid conduits are secured to the frame configured to be removably attached to the first valve, the second valve, and the third valve of the fluid sampling device.

2. The cartridge of claim 1, wherein the valves are pinch valves.

3. The cartridge of claim 1, wherein the cartridge is a sterilized cartridge.

4. The cartridge of claim 1, further comprising a blister-pack surrounding the pump, reservoir, fluid conduits, and fluid fittings.

5. A cartridge for a fluid sampling device for collecting a fluid sample from a test subject, including:
   a pump being moveable in a first direction to draw fluid into the pump and a second direction to expel fluid from the pump;
   a reservoir in fluid communication with the pump;
   a first conduit fluidly connecting the reservoir to a first fluid fitting configured to fluidly connect the cartridge to a tubing having a distal end inserted into the subject;
   a second conduit fluidly connecting the reservoir to a second fluid fitting configured to connect the cartridge to a sample collection component; and
   a third conduit fluidly connecting the reservoir to a third fluid fitting configured to connect the cartridge to a sterile fluid supply;
   wherein the pump is configured to move in the first direction and second direction in response to movement of a portion of the fluid sampling device when the cartridge is operably connected to the fluid sample device and the fluid conduits are configured such that when the cartridge is operably connected to the fluid sampling device, a first valve of the fluid sampling device controls fluid flow in the first fluid conduit, a second valve of the fluid sampling device controls fluid flow in the second fluid conduit, and a third valve of the fluid sampling device controls fluid flow in the third fluid conduit;
   wherein the cartridge includes stationary elements configured to cooperate with valve elements of the fluid sampling device to control fluid flow in the fluid conduits, the valve elements being driven from the fluid sampling device into engagement with the fluid conduits against the stationary elements to restrict or prevent fluid flow through the conduit; and
   wherein the pump, reservoir, and fluid conduits are secured to a frame configured to be removably attached to the first valve, the second valve, and the third valve of the fluid sampling device.

6. A cartridge for a fluid sampling device for collecting a fluid sample from a test subject, including:
   a reservoir;
   a first conduit fluidly connecting the reservoir to a first fluid fitting configured to fluidly connect the cartridge to a tubing having a distal end inserted into the subject;
   a second conduit fluidly connecting the reservoir to a second fluid fitting configured to connect the cartridge to a sample collection component;
   a third conduit fluidly connecting the reservoir to a third fluid fitting configured to connect the cartridge to a sterile fluid supply; and
   a fourth conduit fluidly connecting the reservoir to a fourth fluid fitting configured to connect the cartridge to a pump being moveable in a first direction to draw fluid into the pump and a second direction to expel fluid from the pump;
   wherein the fluid conduits are configured such that when the cartridge is operably connected to the fluid sampling device, a first valve of the fluid sampling device controls fluid flow in the first fluid conduit, a second valve of the fluid sampling device controls fluid flow in the second fluid conduit, and a third valve of the fluid sampling device controls fluid flow in the third fluid conduit;
   wherein the cartridge includes at least one window through a frame configured to allow the first valve of the fluid sampling device to extend through the frame to control fluid flow in the first fluid conduit by applying compressive force to the first fluid conduit, the second valve of the fluid sampling device to extend through the frame to control fluid flow in the second fluid conduit by applying compressive force to the second fluid conduit, and the third valve of the fluid sampling device to extend through the frame to control fluid flow in the third fluid conduit by applying compressive force to the third fluid conduit; and wherein the pump, reservoir, and fluid conduits are secured to the frame configured to be removably attached to the first valve, the second valve, and the third valve of the fluid sampling device.

7. The cartridge of claim 6, wherein the valves are pinch valves.

8. The cartridge of claim 6, wherein the cartridge is a sterilized cartridge.

9. The cartridge of claim 6, further comprising a blister-pack surrounding the reservoir, fluid conduits, and fluid fittings.

10. A cartridge for a fluid sampling device for collecting a fluid sample from a test subject, including:
  a reservoir;
  a first conduit fluidly connecting the reservoir to a first fluid fitting configured to fluidly connect the cartridge to a tubing having a distal end inserted into the subject;
  a second conduit fluidly connecting the reservoir to a second fluid fitting configured to connect the cartridge to a sample collection component;
  a third conduit fluidly connecting the reservoir to a third fluid fitting configured to connect the cartridge to a sterile fluid supply; and
  a fourth conduit fluidly connecting the reservoir to a fourth fluid fitting configured to connect the cartridge to a pump being moveable in a first direction to draw fluid into the pump and a second direction to expel fluid from the pump;
  wherein the fluid conduits are configured such that when the cartridge is operably connected to the fluid sampling device, a first valve of the fluid sampling device controls fluid flow in the first fluid conduit, a second valve of the fluid sampling device controls fluid flow in the second fluid conduit, and a third valve of the fluid sampling device controls fluid flow in the third fluid conduit;
  wherein the cartridge includes stationary elements configured to cooperate with valve elements of the fluid sampling device to control fluid flow in the fluid conduits, the valve elements being driven from the fluid sampling device into contact with the fluid conduits against the stationary elements to restrict or prevent fluid flow through the conduit; and
  wherein the pump, reservoir, and fluid conduits are secured to a frame configured to be removably attached to the first valve, the second valve, and the third valve of the fluid sampling device.

11. A method of collecting a fluid sample from a test subject, the method comprising:
  (a) removably attaching a cartridge to a fluid sampling device including a first valve, a second valve and a third valve, the cartridge comprising:
    a pump being moveable in a first direction to draw fluid into the pump and a second direction to expel fluid from the pump;
    a reservoir in fluid communication with the pump, the reservoir having a first opening and a second opening;
    a first conduit fluidly connecting the reservoir to a first fluid fitting configured to fluidly connect the cartridge to tubing having a distal end inserted into the subject;
    a second conduit fluidly connecting the reservoir to a second fluid fitting configured to connect the cartridge to a sample collection component; and
    a third conduit fluidly connecting the reservoir to a third fluid fitting configured to connect the cartridge to a sterile fluid supply;
    wherein the pump is configured to move in the first direction and second direction in response to movement of a portion of the fluid sampling device when the cartridge is operably connected to the fluid sample device and the fluid conduits are configured such that when the cartridge is operably connected to the fluid sampling device, the first valve of the fluid sampling device controls fluid flow in the first fluid conduit, the second valve of the fluid sampling device controls fluid flow in the second fluid conduit, and the third valve of the fluid sampling device controls fluid flow in the third fluid conduit, each valve having an open state and a closed state; and wherein the fluid sampling device includes a controller for controlling the pump and valve;
  (b) connecting the distal end of the tubing to the subject;
  (c) opening the first valve, and moving the pump in the first direction to draw sample fluid through the first conduit and into the reservoir; thereby forming a sample fluid/sterile fluid interface;
  (d) opening the second valve, and moving the pump in the second direction to force sample fluid from the reservoir through the second conduit to the sample collection component;
  (e) re-opening the first valve, and moving the pump in the second direction to force the sterile fluid out of the first fluid fitting, thereby flushing the first conduit;
  (f) re-opening the second valve, and moving the pump in the second direction to force the sterile fluid out of the second fluid fitting, thereby flushing the second conduit and the sample collection component, (g) opening the third valve, and moving the pump in the first direction to draw the sterile fluid through the third fluid fitting and into the pump through the first opening of the third conduit; and
  (h) removing the cartridge from the fluid sampling device; wherein steps (c)-(g) are executed by the controller.

12. The method of claim 11, wherein the controller repeats steps (c)-(g) a plurality of times in succession.

13. The method of claim 11, wherein the method further comprises prior to step (c):
  actuating the pump to fill the pump with the sterile fluid;
  opening second valve, and actuating the pump to fill the reservoir and the second conduit with the sterile fluid;
  opening the first valve and actuating the pump to fill the first conduit with the sterile fluid;
  coupling the tubing to the first fluid fitting;
  opening the first valve, and actuating the pump to draw a first amount of fluid from the tubing; and
  opening the first valve, and actuating the pump to return the first amount of blood through the tubing to the subject.

14. The method of claim 11, wherein the test subject is an adult human.

15. The method of claim 11, wherein the test subject is a human child.

16. The method of claim 11, wherein the cartridge includes at least one window through a frame, and removably attaching the cartridge the fluid sampling device includes extending the first valve of the fluid sampling device through a window of the at least one window and fitting the first valve around the first conduit, extending the second valve of the fluid sampling device through a window of the at least one window and fitting the second valve around the second conduit, and extending the third valve of the fluid sampling device through a window of the at least one window and fitting the third valve around the third conduit.

17. The method of claim 11, further comprising the steps of:

(i) removably attaching a second cartridge to the fluid sampling device, the second cartridge comprising:
   a pump being moveable in a first direction to draw fluid into the pump and a second direction to expel fluid from the pump;
   a reservoir in fluid communication with the pump, the reservoir having a first opening and a second opening;
   a first conduit fluidly connecting the reservoir to a first fluid fitting configured to fluidly connect the cartridge to tubing having a distal end inserted into the subject;
   a second conduit fluidly connecting the reservoir to a second fluid fitting configured to connect the cartridge to the sample collection component; and
a third conduit fluidly connecting the reservoir to a third fluid fitting configured to connect the cartridge to the sterile fluid supply
wherein the pump of the second cartridge is configured to move in the first direction and second direction in response to movement of the portion of the fluid sampling device when the cartridge is operably connected to the fluid sample device and the fluid conduits of the second cartridge are configured such that when the second cartridge is operably connected to the fluid sampling device, the first valve of the fluid sampling device controls fluid flow in the first fluid conduit, the second valve of the fluid sampling device controls fluid flow in the second fluid conduit, and the third valve of the fluid sampling device controls fluid flow in the third fluid conduit.

* * * * *